United States Patent [19]
Arimatsu et al.

[11] Patent Number: 6,015,398
[45] Date of Patent: Jan. 18, 2000

[54] SYRINGE NEEDLE COATED WITH POLYORGANOSILOXANES

[75] Inventors: Yoshikazu Arimatsu; Takeshi Nizuka, both of Osaka, Japan

[73] Assignee: Nissho Corporation, Osaka, Japan

[21] Appl. No.: 09/075,848

[22] Filed: May 12, 1998

[30] Foreign Application Priority Data

May 12, 1997 [JP] Japan ..................................... 9-121264

[51] Int. Cl.$^7$ ....................................................... A61M 5/32
[52] U.S. Cl. ............................................ 604/272; 604/265
[58] Field of Search ..................................... 604/265, 272

[56] References Cited

U.S. PATENT DOCUMENTS

| | | | |
|---|---|---|---|
| 4,664,657 | 5/1987 | Williamitis et al. ..................... | 604/265 |
| 4,693,936 | 9/1987 | McGregor et al. ...................... | 428/383 |
| 5,087,286 | 2/1992 | Fukuda et al. .......................... | 525/440 |
| 5,283,279 | 2/1994 | Hara et al. .............................. | 524/492 |
| 5,405,691 | 4/1995 | Noda et al. ............................. | 524/588 |
| 5,501,904 | 3/1996 | Noda et al. ............................. | 428/331 |
| 5,505,997 | 4/1996 | Strong et al. ........................... | 427/348 |
| 5,786,032 | 7/1998 | Hughes .................................... | 427/387 |
| 5,844,058 | 12/1998 | Sugama .................................. | 427/435 |

*Primary Examiner*—Wynn Wood Coggins
*Assistant Examiner*—Jennifer R. Sadula
*Attorney, Agent, or Firm*—Kubovcik & Kubovcik

[57] ABSTRACT

A needle which has decreased piercing resistance, which resistance does not increase by repeated piercing and of which a sterilizing means is not limited, is provided by the present invention. The needle is coated on its outside surface with a mixture of (1) a polyorganosiloxane having amino groups at both terminal ends reacted with an alkoxysilane having epoxy groups and (2) a non-reactive polyorganosiloxane which has a lower average degree of polymerization of its siloxane part than that of polyorganosiloxane (1).

9 Claims, No Drawings

SYRINGE NEEDLE COATED WITH POLYORGANOSILOXANES

BACKGROUND OF THE INVENTION

The present invention relates to a needle coated on its surface with polyorganosiloxane.

It is a conventional technique to treat a metal surface with a silicone compound to reduce piercing resistance. For example, Japanese Patent Publication Sho (Tokko-sho) 46-3627 discloses a metal cutting blade having on its surface an adhesive coating material which comprises a siloxane unit having an amino group and an organosiloxane unit. When the adhesive coating material is applied to a needle, the coating material makes it possible to reduce piercing resistance. However, it is a problem that if the needle is used repeatedly, the coating is peeled off because curing of the adhesive material is not sufficient. Such repetition occurs when a liquid medicine is stored in a vial. That is, the needle is used to pierce a rubber lid of a vial to introduce the liquid medicine into a syringe tube, and then the liquid medicine is injected into a human body through the needle. It is also a problem that gamma ray irradiation cannot be applied for sterilization to the needle having the adhesive coating because the piercing resistance of the needle is increased by gamma ray irradiation.

Meanwhile, Japanese Patent Publication Sho (Tokko-sho) 61-35870 discloses a needle coated with a material prepared by a reaction between a reaction product of a silane containing an amino group and a silane containing an epoxy group and a polydiorganosiloxane having silanol group at a terminal end, and cured at room temperature or by heating at 100~150° C. The coating has excellent curing characteristics because it contains silane having an epoxy group. However, piercing resistance of the needle cannot be reduced sufficiently to reduce a patient's pain because the coating is too hard.

Further, Japanese Laid-open Hei (Tokai-hei) 7-178159 discloses coating a needle with a coating agent comprising a specific polyorganosiloxane having amino group and a specific polyorganosiloxane, and treating the surface by a curing method including gamma-ray irradiation. Although the piercing resistance of the needle is reduced when the coating is cured by gamma-ray irradiation, when the coating is cured by methods other than gamma-ray irradiation, the resistance is not necessarily reduced. Therefore, a sterilization method is limited to gamma-ray irradiation.

OBJECT OF THE INVENTION

An object of the present invention is to solve the problems explained above and to provide a needle which can be used repeatedly without an increase in piercing resistance, and for which sterilization methods are not limited.

SUMMARY OF THE INVENTION

The inventors of the present invention have conducted research to solve the problems explained above, and have completed this invention. According to the invention a mixture of (1) a reactant of a polyorganosiloxane having amino groups at both terminal ends and an alkoxysilane containing epoxy groups and (2) a non-reactive polyorganosiloxane having an average polymerization degree of the siloxane part that is not more than that of the polyorganosiloxane (1) having amino groups reacted with epoxy groups of an alkoxysilane, is applied to the surface of a needle.

That is, the present invention relates to a needle coated with a mixture of a first polyorganosiloxane obtained by a reaction of both terminal amino groups thereof with an alkoxysilane containing epoxy groups, and a second non-reactive polyorganosiloxane, the average polymerization degree of siloxane parts of which is not more than that of the first polyorganosiloxane.

DESCRIPTION OF PREFERRED EMBODIMENTS

It is preferred that the average polymerization degree of the polyorganosiloxane prepared by reacting the terminal amino groups at both ends thereof with an alkoxysilane having epoxy groups (hereinafter sometimes referred to as the "reacted polyorganosiloxane") is 10~10,000. It is preferred that the weight ratio of non-reactive polyorganosiloxane to reacted polyorganosiloxane is 1/10~7/10.

The polyorganosiloxane of which at the terminal ends amino groups are reacted with epoxy groups of an alkoxysilane is synthesized from a polyorganosiloxane having silanol groups at the terminal ends. The polyorganosiloxane useful for the present invention is polydimethylsiloxane, polydiethylsiloxane, polymethylphenylsiloxane, or the like. Polydimethylsiloxane is preferred.

That is, a two-step reaction is conducted as explained below. In the first step, polyorganosiloxane having silanol groups at both terminal ends is reacted with alkoxysilane having amino group. Then, in the second step, the reaction product of the first step is reacted with alkoxysilane containing epoxy group. During the first reaction, silanol groups of the polyorganosiloxane are reacted with alkoxysilyl groups of the alkoxysilane having amino group. During the second reaction, amino groups of the reacted alkoxysilane are mainly reacted with epoxy groups of the alkoxysilane containing epoxy group. The obtained polyorganosiloxane has amino groups reacted with epoxy groups at both terminal ends and alkoxysilyl groups.

The alkoxysilane having amino group is preferably one represented by the following formula:

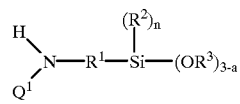

wherein $Q^1$ is a monofunctional group selected from the group consisting of hydrogen, methyl, aminoethyl ($—CH_2—CH_2—NH_2$) and $—CH_2—CH_2—NH—CH_2—CH_2—NH_2$, $R^1$ is a difunctional hydrocarbon group of 1 to 4 carbon atoms, $R^2$ and $R^3$ are each independently a monofunctional hydrocarbon group of 1 to 4 carbon atoms and a is 0 or 1. The following compounds are useful as the alkoxysilane containing amino group in the present invention: N-β(aminoethyl)γ-aminopropylmethyldimethoxysilane, N-β(aminoethyl)γ-aminopropyltriethoxysilane, N-β(aminoethyl)γ-aminopropylmethoxysilane, γ-aminopropyltrimethoxysilane, γ-aminopropylmethyldiethoxysilane, γ-aminopropyltriethoxysilane, and the like.

The alkoxysilane containing epoxy group is preferably one represented by the following formula:

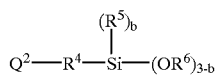

wherein $Q^2$ is glycidoxy or epoxycyclohexyl, $R^4$ is a difunctional hydrocarbon group of 2 to 4 carbons, $R^5$ and $R^6$ are each independently a monofunctional hydrocarbon group of 1 to 4 carbon atoms, and b is 0 or 1. The following compounds are useful as the alkoxysilane containing epoxy group in the present invention: γ-glycidoxypropyltrimethoxysilane, γ-glycidoxypropylmethyldiethoxysilane, γ-glycidoxypropyltriethoxysilane, β-(3,4-epoxycyclohexyl)ethyltrimethoxysilane and the like.

Instead of the reaction described above, an alkoxysilane containing amino group can be reacted with an alkoxysilane containing epoxy group in the first step of preparation. Then, as the second step, the reaction product of the first step can be reacted with a polyorganosiloxane having silanol groups at both terminal ends. In this procedure, during the first reaction amino groups of the alkoxysilane containing amino group react with epoxy groups of the alkoxysilane containing epoxy group. During the second reaction, alkoxysilyl groups of the reaction product of the first step react with silanol groups of the polyorganosiloxane having silanol groups at both terminal ends. The desirable composition can be prepared by any other known methods. It is, of course, not limited to the methods described above.

The obtained composition is mixed with non-reactive polyorganosiloxane, and is diluted with a solvent to 2~9% and, preferably, 3~6% by weight of nonvolatile content. If the solid concentration of the mixture is less than 2% by weight, the piercing resistance become high. If the solid concentration of the mixture is more than 9% by weight, it is difficult to provide a uniform coating on the surface of the needle, and the coating tends to stick on a rubber lid of a vial when the coated needle is used to pierce the lid.

The average polymerization degree of the siloxane part of the non-reactive polyorganosiloxane is less than that of the siloxane part of the polyorganosiloxane obtained by the reaction of an alkoxysilane containing epoxy group to its amino groups at the both terminal ends. If the average polymerization degree of the non-reactive polyorganosiloxane is higher than that of the siloxane part of the reacted polyorganosiloxane, it is difficult for the cross-linking of polyorganosiloxane to progress, and a good cross-linked polymer is not formed. If the polymer is applied to a needle, piercing resistance is high, and the needle does not have good piercing properties for repeated use. The average degree of polymerization of the non-reactive polyorganopolysiloxane is, preferably, 10~100% and, more preferably, 50~80% of the average degree of polymerization of the reacted polyorganosiloxane.

A syringe needle of this invention is prepared by dipping a needle in a coating solution, i.e., a diluted mixture of reacted polyorganosiloxane and non-reactive polyorganosiloxane, and is left to stand at room temperature. While the needle is left at room temperature, alkoxysilyl groups attach to the surface of the needle by condensation reaction, and the alkoxysilyl groups are condensed with each other to form cross-linked polymer. An organic acid, for example, acetic acid and the like, may be added to the mixture to accelerate reaction. It is also possible to raise the temperature to about 100° C. for about one hour to accelerate the reaction. The non-reactive polyorganosiloxane exists in the cross-linked polymer without participating in the reaction, and provides good lubricating property to the needle. That is, the needle coated with a cross-linked polymer of the polyorganosiloxane having amino groups at both terminal ends reacted with alkoxysiloxane having epoxy groups, and with non-reactive polyorganosiloxane is prepared. As a needle there can be used an injection needle, a winged needle, a retained needle or the like. A needle which can be used for this invention is not limited.

It is preferable that an average degree of polymerization of the siloxane part of the polyorganosiloxane having amino groups at both terminal ends and reacted with alkoxysilane having epoxy groups, in the mixture of polyorganosiloxane having amino groups at the both terminal ends and reacted with alkoxysilane having epoxy groups and the non-reactive polyorganosiloxane, is in a range of 10~10,000. If the average degree of polymerization of the siloxane part is less than 10, it is difficult for crosslinking to occur in the presence of the non-reactive polyorganosiloxane and it tends not to form a preferable crosslinked polymer. If the average degree of polymerization of the siloxane part is more than 10,000, there is a tendency that alkoxysilyl groups are not reacted with each other, and it is unlikely to obtain a preferable crosslinked polymer. It is further preferable that the average degree of polymerization is in a range of 10~1,000. It is preferred that the ratio of the non-reactive polyorganosiloxane to the polyorganosiloxane having amino groups at both terminal ends and reacted with alkoxysilane having epoxy groups is 1/10~7/10 by weight. If the ratio is less than 1/10, piercing resistance tends to be increased. If the ratio is more than 7/10, the needle has inferior piercing properties.

The needle coated with such crosslinked polymer has not only reduced piecing resistance but also stability of the coating for repeated use of the needle. That is, the coating does not peel easily by repeated use of the needle. Changes of properties, including piercing property and discoloration, with time of the needle of the invention do not occur. The coating does not elute in blood because it is a crosslinked polymer attached to the metal surface of the needle. Even if the needle is exposed to gamma rays, the piercing resistance is not increased since the coated polymer has been cured sufficiently. When the needle is contacted with ethylene oxide gas, the piercing resistance is not increased but decreased (See Table 1). Thus, a sterilizing method for the needle of the present invention is not limited to radiation.

The following examples illustrate embodiments of the present invention.

EXAMPLE 1

5 parts by weight of a silicone compound having amino groups at both terminal ends and alkoxysilyl groups (MDX 4-4159, Dow Corning Inc., average degree of polymerization: ca. 70) and 0.2 parts by weight of γ-glycidoxypropylmethyldimethoxysilane (KBM-402, Shin-etsu Chemical Co., Ltd.) were reacted in 10 parts by weight of toluene at 80° C. for 3 hours. After completion of the reaction, 2.5 parts by weight of polydimethylsiloxane having a viscosity of 50 cSt (KF-96 50 cSt, Shin-etsu Chemical Co., Ltd., average degree of polymerization: ca. 50) and 82.3 parts by weight of dichloropentafluoropropane (AK-225, Asahi Glass Co., Ltd.) were added to obtain a colorless transparent coating liquid. A 21G injection needle was dipped in this coating liquid and heat treatment was conducted at 100° C. for 1 hour.

The obtained needle was pricked vertically into a natural rubber sheet having a thickness of 1.5 mm and a hardness of 30 at a crosshead speed of 100 mm/min. The resistance value was measured by a universal tester (AG-500, Shimazu Corp.) The resistance when the top of the needle pierced the natural rubber sheet (first and fifth attempts) and degree of adherence of silicone on the surface of the sheet are shown in Table 1.

EXAMPLE 2

0.1 part by weight of y-aminopropyltriethoxysilane (KBE-903, Shin-etsu Chemical Co., Ltd.) and 0.1 part by weight of γ-glycidoxypropylmethyldimethoxysilane (KBM-402, Shin-etsu Chemical Co., Ltd.) were reacted at 80° C. for 3 hours. A mixture of 3 parts by weight of polydimethylsiloxane (average degree of polymerization: ca. 300) having silanol groups at both terminal ends and 10 parts by weight of toluene were added to the compound obtained by the reaction, and were reacted at 80° C. for 12 hours. After completion of the reaction, 3 parts by weight of polydimethylsiloxane having a viscosity of 350 cSt(DC-360 350 cSt, Dow Corning Corp., average degree of polymerization: ca. 200), 5 parts by weight of n-decane and 78.8 parts by weight of dichloropentafluoropropane were added to obtain a colorless, transparent coating solution. A 21G syringe needle was dipped in the coating solution and heat-treated at 100° C. for 1 hour. The prepared needle was tested in the same way as explained in Example 1. Obtained results are shown in Table 1.

EXAMPLE 3

A 21G needle was dipped in the same coating liquid as in Example 2 and sterilized with ethylene oxide gas instead of a one hour heat treatment at 100° C. The treated needle was tested in the same way as in Example 1, and the results are shown in Table 1.

EXAMPLE 4

A 21G needle was dipped in the same coating liquid as in Example 2 and sterilized by gamma ray irradiation instead of a heat treatment at 100° C. for one hour. The gamma ray treated needle was tested in the same way as in Example 1, and the results are shown in Table 1.

COMPARATIVE EXAMPLE 1

Polydimethylsiloxane having a viscosity of 12,500 cSt (DC-360 12,500 cSt, Dow Corning Inc., average degree of polymerization: ca. 850) was used instead of the polydimethylsiloxane having a viscosity of 500 cSt in Example 1. The prepared injection needle was tested in the same way as in Example 1 and the results are shown in Table 1.

COMPARATIVE EXAMPLE 2

Polydimethylsiloxane having a viscosity of 12,500 cSt (DC-360 12,500 cSt, Dow Corning Inc., average degree of polymerization: ca. 850) was used instead of the polydimethylsiloxane having a viscosity of 350 cSt in Example 2, and the results are shown in Example 1.

TABLE 1

|  | Piercing resistance (g) | | Adherence of |
| --- | --- | --- | --- |
|  | 1st time | 5th time | silicone |
| Example 1 | 11.3 | 11.5 | Minor |
| Example 2 | 9.1 | 9.7 | Very minor |
| Example 3 | 8.5 | 9.2 | Very minor |
| Example 4 | 9.3 | 9.5 | Very minor |
| Comp. Example 1 | 14.7 | 23.5 | Very major |
| Comp. Example 2 | 11.5 | 17.3 | Major |

As is apparent from the results shown in Table 1, the needles of the comparative examples have high piercing resistance and the resistance increased after repeated piercing. The amount of silicone affixed to the flat rubber was also significant with the needles of the comparative examples. The needles of the present invention have low piercing resistance, and the resistance does not increase by repeated piercing. The amount of silicone affixed to the flat rubber was less than that of the needles of the comparative examples. Further, the piercing resistance is not increased by sterilization with ethylene oxide gas or gamma ray irradiation.

Effect of the Invention

The present invention provides a needle which has a decreased piercing resistance, and which resistance does not increase by repeated piercing. Furthermore, means for sterilizing the needle is not limited.

What is claimed is:

1. A coated syringe needle comprising a syringe needle coated on its surface with a mixture of:
   (1) a first polyorganosiloxane selected from the group consisting of
      (i) a reaction product of (a) a polyorganosiloxane having amino groups at both terminal ends and alkoxysilyl groups with (b) an epoxy group-containing alkoxysilane and
      (ii) a reaction product of (a) a polyorganosiloxane having silanol groups with (b) another reaction product of an organosiloxane having amino groups at terminal ends with an epoxy group-containing alkoxysilane and
   (2) a second non-reactive polyorganosiloxane, said second polyorganosiloxane having a lower average degree of polymerization of siloxane part than that of said first polyorganosiloxane.

2. A coated syringe needle according to claim 1, wherein the average degree of polymerization of siloxane part of said polyorganosiloxane (1) is 10~10,000.

3. A coated syringe needle according to claim 1, wherein the amount of said non-reactive polyorganosiloxane (2) in said mixture is 1/10~7/10 by weight of the amount of the polyorganosiloxane (1).

4. A coated syringe needle according to claim 2, wherein the amount of said non-reactive polyorganosiloxane (2) in said mixture is 1/10~7/10 by weight of the amount of the polyorganosiloxane (1).

5. A coated syringe needle according to claim 1, wherein the epoxy group-containing alkoxysilane is γ-glycidoxypropylmethyl dimethoxysilane.

6. A coated syringe needle according to claim 1, wherein the second polyorganosiloxane is polydimethylsiloxane.

7. A coated syringe needle according to claim 1, wherein the polyorganosiloxane having amino groups at both terminal ends and alkoxysilyl groups of the reaction product (i) is a polydimethylsiloxane having amino groups at both terminal ends and methoxysilyl groups.

8. A coated syringe needle according to claim 1, wherein the polyorganosiloxane having silanol groups of the reaction product (ii) is a polydimethylsiloxane having silanol groups at both terminal end.

9. A coated syringe needle according to claim 1, wherein the organosiloxane having amino groups at terminal ends of the reaction product (ii) is γ-aminopropyltriethoxysilane.

* * * * *

UNITED STATES PATENT AND TRADEMARK OFFICE
CERTIFICATE OF CORRECTION

PATENT NO. : 6,015,398
DATED : January 18, 2000
INVENTOR(S) : Yoshikazu ARIMATSU et al.

It is certified that error appears in the above-indentified patent and that said Letters Patent is hereby corrected as shown below:

Column 5, line 25: "γ-aminopropyltriethoxysilane" should read --γ-aminopropyltriethoxysilane--.

Claim 1, lines 11 and 12: "organosiloxane having amino groups at terminal ends" should read --alkoxysilane containing amino groups--.

Claim 9, line 2: "organosiloxane having amino groups at terminal ends" should read --alkoxysilane containing amino groups--.

Signed and Sealed this

First Day of May, 2001

Attest:

NICHOLAS P. GODICI

*Attesting Officer*         *Acting Director of the United States Patent and Trademark Office*